United States Patent
Goettel et al.

(10) Patent No.: US 8,834,580 B2
(45) Date of Patent: Sep. 16, 2014

(54) AMMONIUM HYDROXIDE-FREE HAIR DYE COMPOSITIONS CONTAINING A BUFFER SYSTEM

(75) Inventors: Otto Goettel, Osio Sotto (IT); Johann Aeby, Osio Sotto (IT); Alberto Finazzi, Osio Sotto (IT)

(73) Assignee: Alfa Parf Group S.p.A., Bologna (IT)

( * ) Notice: Subject to any disclaimer, the term of this patent is extended or adjusted under 35 U.S.C. 154(b) by 0 days.

(21) Appl. No.: 14/115,240

(22) PCT Filed: May 18, 2012

(86) PCT No.: PCT/IB2012/052511
§ 371 (c)(1),
(2), (4) Date: Nov. 12, 2013

(87) PCT Pub. No.: WO2012/156953
PCT Pub. Date: Nov. 22, 2012

(65) Prior Publication Data
US 2014/0082856 A1    Mar. 27, 2014

(30) Foreign Application Priority Data
May 18, 2011   (IT) .............................. MI2011A0883

(51) Int. Cl.
*A61Q 5/10*    (2006.01)
*A61K 8/49*    (2006.01)
*A61K 8/41*    (2006.01)

(52) U.S. Cl.
CPC ... *A61K 8/41* (2013.01); *A61K 8/49* (2013.01); *A61Q 5/10* (2013.01)
USPC ....................................... 8/405; 8/406; 8/604

(58) Field of Classification Search
USPC .............................................. 8/405, 406, 604
See application file for complete search history.

(56) References Cited

U.S. PATENT DOCUMENTS 5,798,095 A      8/1998   Racky
2010/0229314 A1*  9/2010  Takiguchi ........................ 8/405

FOREIGN PATENT DOCUMENTS

| DE | 19527121 | 1/1997 |
|----|----------|--------|
| DE | 19961273 | 7/2001 |
| WO | 9606544  | 3/1996 |

OTHER PUBLICATIONS

International Search Report issued in counterpart PCT Application No. PCT/IB2012/052511, (Nov. 2012).
Written Opinion of International Searching Authority issued in counterpart PCT Application No. PCT/IB2012/052511, (2012).

* cited by examiner

*Primary Examiner* — Eisa Elhilo
(74) *Attorney, Agent, or Firm* — Silvia Salvadori, P.C.

(57) ABSTRACT

The present invention relates to oxidative hair colorants containing a buffer system consisting of saccharine and at least one alkanolamine. The colorants are free of ammonium hydroxide and sources of ammonia.

10 Claims, No Drawings

AMMONIUM HYDROXIDE-FREE HAIR DYE COMPOSITIONS CONTAINING A BUFFER SYSTEM

This application is a U.S. national stage of PCT/IB2012/052511 filed on May 18, 2012, which claims priority to and the benefit of Italian Application No. MI2011A000883 filed on May 18, 2011, the contents of which are incorporated herein by reference in their entirety.

FIELD OF INVENTION

The present invention relates to oxidative keratinic dyeing compositions, free of ammonium hydroxide and sources of ammonia, containing a buffer system.

PRIOR ART

The desire to change the colour of natural and synthetic fibres has developed over the years. In particular, hair dyeing in humans is motivated by changes in style and fashion.

There are currently numerous trends in hair dyeing. In the past, the hair was mainly dyed to conceal areas of grey hair, whereas there is now increased demand to have a hair colour based on fashion as an expression of the personality.

Now, as then, two hair dyeing methods are widely used. One is the permanent system, which involves dyeing the hair with colourants containing direct non-oxidative dyes (often called toners). Although both the colouring capacity of the dyes used for this purpose, and their ability to remain on the hair as long as possible, are optimised, the shade of colour gradually fades with each wash. Depending on the product used and the hair type, these shades do not generally last for more than 10 washes. Although they are designed for direct dyeing, some of these dyes can also be applied in the presence of hydrogen peroxide to intensify the resulting shade and obtain better root to tip evenness.

Besides the permanent system, oxidative dyes have achieved considerable importance in cosmetics in the field of conventional hair dyes. The colour is created by the reaction of certain primary intermediates and couplers in the presence of an oxidant. In addition to the creation of colour effects, very strict requirements are imposed for oxidative dyes designed for human hair treatment. Firstly, the dyes must be innocuous from the toxicological and dermatological standpoint and must not be sensitising. It must also be possible, by combining primary intermediates and suitable couplers, to produce a wide range of different shades. Moreover, the hair dyes produced must possess good resistance to washing, light resistance, sweat resistance, resistance to permanent treatments, resistance to acids, resistance to bases and resistance to abrasion. In any event, these hair dyes must remain stable for at least four to six weeks under normal everyday conditions.

The oxidative system is based on the reaction of primary intermediates with couplers; both types of molecules are practically colourless. In the presence of air or oxidants such as hydrogen peroxide, primary aromatic amines with a hydroxy or additional amino group at the para or ortho position, substituted or unsubstituted, react with resorcinol, m-aminophenol, m-phenylenediamine or 1-naphthol couplers. Some years ago, a novel primary intermediate, a substituted 4,5-diaminopyrazole, was introduced to provide deep red shades with the majority of couplers commonly used.

As the size of the dye molecules formed is larger than the size of the highly diffusible starting primary intermediates and couplers, no significant fading takes place after dyeing. An oxidative hair dye that produces a very lasting shade is therefore also called the "permanent" system.

The base used to regulate the pH was preferably ammonium hydroxide. The advantage of using ammonium hydroxide is that the combination with hydrogen peroxide gives a slight lightening to the hair. During the process, the lightening proceeds in parallel with the colouring of the hair. In this respect, the lightening effect is crucial for evenness.

However, the volatility of ammonia generates the characteristic unpleasant odour which is considered to be a considerable drawback. In order to deal with this problem effectively, manufacturers of hair colourants have sought to replace ammonium hydroxide with short-chain amines, in particular alkanolamines. As said amines are virtually odourless, hair dyes completely free of undesirable odours could be produced. Products have appeared over recent years which contain alkanolamines as alkalisers. The odour problems seemed to have been solved by using said alkalisers, but the results are unsatisfactory due to the absence of the lightening effect at lower concentrations and potential irritation at higher concentrations.

The first problem is that the lightening effect is poor if dermatologically acceptable amounts are used.

The amount required to obtain the lightening effect should be much higher, namely equimolar to the ammonia of level 3 dyes, causing severe irritation or even damage to the skin.

Secondly, alkanolamines are not volatile under normal conditions of application. The hair structure is therefore gradually damaged by alkanolamine residues, especially after frequent applications.

Moreover, increased concentrations of alkanolamines in combination with hydrogen peroxide can cause irritation or burning to individuals with a sensitive scalp.

The use of alkanolamines is therefore to some extent limited to hair dyes used to obtain darker shades than the original hair colour. In these cases, the main objective is to cover grey hair.

These oxidative dyes without a lightening effect are also called "permanent" dyes.

In order to minimise odour while keeping the best possible lightening effect, ammonium hydroxide has been replaced by ethanolamine in most cases. Although the concentration of ammonium hydroxide has been reduced, ammonia is distinctly perceptible even at low concentrations. Moreover, as described in DE19527121, a low but continual reduction in pH values has been observed.

In the past, a different approach was proposed to solve the problem of the ammonia odour, which involves using short-chain amines in combination with amino acids. As disclosed in DE19527121, it has been observed that higher levels of amino acids, among which lysine and arginine were expressly cited, often lead to instability of the colourants and separation of the phases. This point is particularly critical for retail products, as consumers can equate minor changes in the appearance of the colourant with deterioration of the product; products which are not sufficiently stable under various storage and temperature conditions can therefore be difficult to commercialize. For this reason the amount of amino acids was limited to 6%, as emulsions are unable to maintain higher amounts of amino acids in solution for a long period of time.

In the meantime, alanine is no longer widely used, and has mainly been replaced by the less expensive glycine.

However, as in the literature regarding the stability of amino acids in the presence of strong oxidants is considered, the possibility that amino acids are insufficiently inert under the conditions commonly present in active mixtures, in other words in the presence of hydrogen peroxide in a basic environment, cannot be ruled out.

Numerous citations relating to the stability of amino acids can be found, for example, in the "Beilstein Handbook of Organic Chemistry"; a review of the articles relating to the stability of amino acids can be found in system number 364, vol. 4, E IV, p. 2351, "Chemisches Verhalten". In the case of glycine, it has been found that formaldehyde, among other degradation products, is formed under strong oxidising conditions.

For this reason there is still a continuous need to find agents and combinations of agents that catalyse the lightening effect on the hair fibres during the dyeing process. Moreover, cosmetic compositions should be free of ammonium hydroxide and sources of ammonia, such as ammonium chloride, ammonium sulphate, ammonium nitrate, ammonium phosphate, ammonium acetate, ammonium carbonate, ammonium bicarbonate, ammonium carbamate, ammonium percarbonate and mixtures thereof.

SUMMARY OF THE INVENTION

The present invention relates to an oxidative hair colour compositions comprising a buffer system consisting of saccharine and at least one alkanolamine.

DETAILED DESCRIPTION OF THE INVENTION

The purpose of the present invention is to find novel colourants having a performance comparable to that of colourants based on ammonium hydroxide, without the above-mentioned drawbacks associated with odour.

The main objective is therefore to provide a system free of ammonium hydroxide, ammonium salts and amino acids, which allows a very delicate treatment to provide lightening and dye the hair. Moreover, the pH of ready-for-use dyes should below 11.

It has now surprisingly been found that the above-mentioned problems can be solved by an ammonia-free colour composition with excellent dyeing performance based on a buffer consisting of a combination of saccharine and at least one alkanolamine, so that the balance indicated in equation (I) is formed.

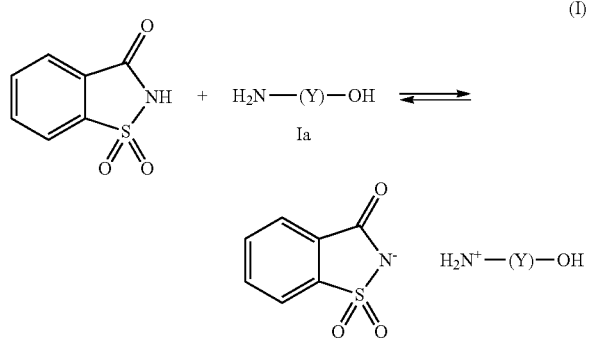

The use of saccharine in different cosmetic compositions, mainly in the form of water-soluble sodium salt, is known. Saccharine has been used as co-agent for various purposes, for example as additive in body care compositions such as toothpastes, skin and hair care compositions, hair styling compositions, permanent wave compositions, straighteners, level 2 bleaching compositions (EP1759684A1), and compositions that prevent decolorizing (KR102004079800A).

In oxidative hair dyes, alkyltrimethylammonium quaternary salts have been used as cationic components for active treatment in compositions based on ammonium hydroxide wherein the saccharine anion served as counterion (GB1097269).

The application of glycylglycine and glycylglycylglycine in combination with aromatic sulphonic acids or derivatives thereof, for example sulphimides like saccharine (such as sodium salts) have also been described as useful in oxidative colourants to give body to fine, damaged hair (EP2201931A1).

The present invention therefore relates to cosmetic colourants for oxidative dyeing of keratin fibres comprising a colouring composition containing primary intermediates and couplers in an aqueous carrier and a buffer system consisting of a combination of saccharine and at least one alkanolamine. Alkanolamine (an alkalinising agent) is a primary amine of general formula Ia wherein Y represents a spacer group consisting of a straight or branched aliphatic diradical, comprising 2 to 5 carbon atoms optionally substituted by one or two further hydroxy groups. Some preferred examples of compounds of general formula Ia are monoethanolamine (MEA), 1-amino-2-propanol, 2-amino-2-methyl-propanol (AMP), 2-amino-2-methyl-1,3-propanediol, 2-amino-2-ethyl-1,3-propanediol and tris(hydroxymethyl)-aminomethane (tromethamine, Tris).

The amount of alkanolamine can range between 0.1 and 17% by weight, preferably between 2 and 10% by weight.

The alkanolamine can be present in the free base form or salt form.

Due to its favourable solubility properties, saccharine can be used in cosmetic compositions, after neutralisation with alkanolamines, in a very wide range. The amount of saccharine, expressed as % by weight of free acid, can preferably range from 0.1 to 17% by weight, more preferably from 1 to 10% by weight, and most preferably from 2 to 6% by weight.

Saccharine can be used in free acid form or salt form.

In the oxidative hair colourant, saccharine and at least one alkanolamine can both be present in free form or both in salt form, or the saccharine can be in free form and at least one alkanolamine can be in salt form, or vice versa.

Saccharine, as acid species in the buffer system, is preferably used in its free acid form, and alkanolamine is preferably used in its free base form.

According to a preferred embodiment due to its very favourable properties, the molar ratio in oxidative dyes between alkalinising agent and saccharine ranges between 1:1 and 10:1, and most preferably between 1:1 and 5:1.

The pH values of the dye can be varied between 8 and 11, preferably between 9 and 10, by varying the amount of alkanolamine selected.

Although the use of ammonium hydroxide is not part of the present invention, the addition of ammonium hydroxide as an auxiliary base is not expressly excluded.

The cosmetic dyes according to the present invention are preferably in the form of solutions, emulsions, creams, gels, aerosol foams, pump foams and squeeze foams.

Primary intermediates, common dyes and known couplers can be used as constituents to form the colourants.

Examples of precursors suitable for use according to the present invention, which can act as primary intermediates, are 1,4-diamino-benzene (p-phenylenediamine); 1,4-diamino-2-methyl-benzene (p-toluylenediamine); 1,4-diamino-2,6-dimethyl-benzene; 1,4-diamino-3,5-diethyl-benzene; 1,4-diamino-2,5-dimethyl-benzene; 1,4-diamino-2,3- dimethylbenzene; 2-chloro-1,4-diaminobenzene; 1,4-diamino-2-(thiophen-2-yl)benzene; 1,4-diamino-2-(thiophen-3-yl)benzene; 1,4-diamino-2-(pyridin-3-yl) benzene; 2,5-diaminobiphenyl; 1,4-diamino-2-methoxymethyl-benzene; 1,4-diamino-2-aminomethylbenzene; 1,4-diamino-2-hydroxymethyl-benzene; 1,4-diamino-2-(2-hydroxyethoxy)benzene; 2-(2-(acetylamino)ethoxy)-1,4-diaminobenzene; 4-phenylamine-aniline; 4-dimethylamino-aniline; 4-diethylamine-aniline; 4-dipropylamine-aniline; 4-[ethyl(2-hydroxyethyl)amino]-aniline; 4-[di(2-hydroxyethyl)amino]-aniline; 4-[di(2-hydroxyethyl)amino]-2-methyl-aniline; 4-[(2-methoxyethyl) amino]-aniline; 4-[(3-hydroxypropyl)amino]-aniline; 4-[(2,3-dihydroxypropyl)amino]-aniline; 1,4-diamino-2-(2-hydroxyethyl)-benzene; 1,4-diamino-2-(1-methylethyl)-benzene; 1,3-bis[(4-aminophenyl)(2-hydroxyethyl)amino]-2-propanol; 1,4-bis[(4-amino-phenyl)amino]-butane; 1,8-bis(2,5-diaminophenoxy)-3,6-dioxaoctane; 4-amino-phenol; 4-amino-3-methyl-phenol; 4-amino-3-(hydroxymethyl)-phenol; 4-amino-3-fluoro-phenol; 4-methylamino-phenol; 4-amino-2-(aminomethyl)-phenol; 4-amino-2-(hydroxymethyl)-phenol; 4-amino-2-fluorophenol; 4-amino-2-[(2-hydroxyethyl)amino]methylphenol; 4-amino-2-methyl-phenol; 4-amino-2-(methoxymethyl)-phenol; 4-amino-2-(2-hydroxyethyl)-phenol; 5-aminosalicylic acid; 2,5-diamino-pyridine; 2,4,5,6-tetraamino-pyrimidine; 4,5-diamino-1-(2-hydroxyethyl)-1H-pyrazole; 4,5-diamino-1-(1-methylethyl)-1H-pyrazole; 4,5-diamino-1-[(4-methylphenyl)methyl]-1H-pyrazole; 1-[(4-chlorophenyl) methyl]-4,5-diamino-1H-pyrazole; 4,5-diamino-1-methyl-1H-pyrazole; 2-aminophenol; 2-amino-6-methylphenol; and 2-amino-5-methylphenol.

Examples of couplers suitable for use according to the present invention are 2,6-diamino-pyridine; 2-amino-4-[(2-hydroxyethyl)amino]anisole; 2,4-diamino-1-fluoro-5-methylbenzene; 2,4-diamino-1-methoxy-5-methylbenzene; 2,4-diamino-1-ethoxy-5-methyl-benzene; 2,4-diamino-1-(2-hydroxyethoxy)-5-methylbenzene; 2,4-di[(2-hydroxyethyl) amino]-1,5-dimethoxybenzene; 2,3-diamino-6-methoxy-pyridine; 3-amino-6-methoxy-2-(methylamino)pyridine; 2,6-diamino-3,5-dimethoxypyridine; 3,5-diamino-2,6-dimethoxy-pyridine; 1,3-diaminobenzene; 2,4-diamino-1-(2-hydroxyethoxy)benzene; 1,3-diamino-4-(2,3-hydroxypropoxy)-benzene; 2,4-diamino-1,5-di(2-hydroxyethoxy)-benzene; 1-(2-aminoethoxy)-2,4-diaminobenzene; 2-amino-1-(2-hydroxyethoxy)-4-methylaminobenzene; 2,4-diaminophenoxyacetic acid ester; 3-[di(2-hydroxyethyl) amino]aniline; 4-amino-2-di[(2-hydroxyethyl)amino]-1-ethoxy-benzene; 5-methyl-2-(1-methylethyl)phenol; N-(3-dimethylamino-phenyl)-urea; 3-[(2-hydroxyethyl)amino] aniline; 3-[(2-aminoethyl)amino]aniline; 1,3-di(2,4-diaminophenoxy)propane; di(2,4-diaminophenoxy) methane; 1,3-diamino-2,4-dimethoxybenzene; 2,6-bis(2-hydroxyethyl)aminotoluene; 4-hydroxyindole; 3-dimethylaminophenol; 3-diethylaminophenol; 5-amino-2-methylphenol; 3-amino-2,6-dimethylphenol; 5-amino-4-fluoro-2-methyl-phenol; 5-amino-4-methoxy-2-methylphenol; 5-amino-4-ethoxy-2-methylphenol; 3-amino-2,4-dichlorophenol; 5-amino-2,4-dichlorophenol; 3-amino-2-methyl-phenol; 3-amino-2-chloro-6-methylphenol; 3-aminophenol; 2-[(3-hydroxyphenyl)-amino]acetamide; 5-[(2-hydroxyethyl)amino]-4-methoxy-2-methylphenol; 5-[(2-hydroxyethyl)amino]-2-methylphenol; 3-[(2-hydroxyethyl)-amino]-phenol; 3-[(2-methoxyethyl)amino]-phenol; 5-amino-2-ethyl-phenol; 5-amino-2-methoxyphenol; 2-(4-amino-2-hydroxyphenoxy)ethanol; 5-[(3-hydroxypropyl) amino]-2-methylphenol; 3-[(2,3-dihydroxypropyl)amino]-2-methylphenol; 3-[(2-hydroxyethyl)amino]-2-methylphenol; 2-amino-3-hydroxypyridine; 5-amino-4-chloro-2-methylphenol; 1-naphthol; 2-methyl-1-naphthol; 1,5-dihydroxynaphthalene; 1,7-dihydroxynaphthalene; 2,3-dihydroxynaphthalene; 2,7-dihydroxy-naphthalene; 2-methyl-1-naphthol-acetate; 1,3-dihydroxybenzene; 1-chloro-2,4-dihydroxy-benzene; 2-chloro-1,3-dihydroxybenzene; 1,2-dichloro-2,4-dihydroxy-4-methylbenzene; 1,5-dichloro-2,4-dihydroxybenzene; 1,3-dihydroxy-2-ethyl-benzene; 3,4-methylenedioxy-phenol; 3,4-methylenedioxy-aniline; 6-bromo-1-hydroxy-3,4-methylene-dioxybenzene; 3,4-diaminobenzoic acid; 3,4-dihydroxy-6-hydroxy-1,4(2H)benzoxazine; 6-amino-3,4-dihydro-1,4(2H)-benzoxazine; 3-methyl-1-phenyl-5-pyrazolone; 5,6-dihydroxyindole; 5,6-dihydroxyindoline; 5-hydroxyindole; and 6-hydroxyindole.

The primary intermediates and couplers can both be used as free bases or also in the form of their physiologically acceptable salts, with inorganic or organic acids such as hydrochloric acid, sulphuric acid, phosphoric acid, lactic acid or citric acid.

The total amount of the combination of primary intermediates and couplers in the dye according to the invention preferably ranges between approx. 0.01 and 20% by weight, more preferably ranges between approx. 0.02 and 10% by weight, and most preferably ranges between approx. 0.2 and 6.0% by weight.

The primary intermediate and the coupler are generally used in approximately equimolar amounts, but it is not necessarily a drawback if the primary intermediate is present in lower or higher amounts than equimolar amount compared with the coupler.

The colourant according to the invention can also contain at least one further intermediate colouring, such as 6-amino-2-methylphenol and 2-amino-5-ethylphenol.

Although a wide range of shades can be obtained with the combination of primary intermediates and couplers, it may be necessary to add direct dyes to the oxidative dyes to obtain bright highlights on dry hair. Some of these dyes are also called "booster" dyes. The direct dyes which can be used according to the invention are preferably selected from direct neutral, acidic or cationic nitrobenzene dyes; direct neutral, acidic or cationic azo dyes; neutral, acidic or cationic quinones, and in particular direct anthraquinone dyes, direct azine dyes, direct triarylmethane dyes, direct indoamine dyes and direct natural dyes.

These direct colouring compounds can be, for example:
aromatic nitro dye compounds such as:
2-amino-3-nitrophenol; 2-[(2-hydroxyethyl)amino]-1-methoxy-5-nitrobenzene; 1-(2-hydroxyethoxy)-3-methylamino-4-nitrobenzene; 2,3-(dihydroxypropoxy)-3-methylamino-4-nitrobenzene; 1-[(2-ureidoethyl)amino]-4-nitrobenzene; 4-[(2-hydroxyethyl)amino]-3-nitro-1-methylbenzene; 1-[(2-hydroxyethyl)amino]-2-nitrobenzene (HC yellow No. 2); 1-(2-hydroxyethoxy)-2-[(2-hydroxyethyl)amino]-5-nitrobenzene (HC yellow No. 4); 1-amino-2-[(2-hydroxyethyl)amino]-5-nitrobenzene (HC yellow No. 5); 4-[(2,3-dihydroxypropyl)amino]-3-nitro-1-trifluoromethyl-benzene (HC yellow No. 6); 3-[(2-aminoethyl)amino]-1-methoxy-4-nitrobenzene hydrochloride (HC yellow No. 9); 1-chloro-2,4-bis-[(2-hydroxyethyl)amino]-5-nitrobenzene (HC yellow No. 10); 2-[(2-hydroxyethyl)amino]-5-nitrophenol (HC yellow No. 11); 1-chloro-4-[(2-hydroxyethyl) amino]-3-nitrobenzene (HC yellow No. 12); 4-[(2-hydroxyethyl)amino]-3-nitro-1-trifluoromethylbenzene (HC yellow No. 13); 4-[(2-hydroxyethyl)amino]-3-nitro-benzonitrile (HC yellow No. 14); 4-[(2-hydroxyethyl)amino]-3-nitro-benzamide (HC yellow No. 15); 1,4-diamino-2-nitrobenzene; 1,4-bis[(2-hydroxyethyl)amino]-2-nitrobenzene; 2-amino-4,6-dinitro-phenol; 4-amino-3-nitrophenol; 1-amino-5-chloro-4-[(2-hydroxyethyl)-amino]-2-nitrobenzene; 4-[(2-hydroxyethyl)amino]-3-nitrophenol; 1-[(2-aminoethyl)amino]-4-(2-hydroxyethoxy)-2-nitrobenzene (HC orange No. 2); 4-(2,3-dihydroxypropoxy)-1-[(2-hydroxyethyl)amino]-2-nitrobenzene (HC orange No. 3); 2-[(2-hydroxyethyl)amino]-4,6-dinitro-phenol; 4-ethylamino-3-nitrobenzoic acid; 2-[(4-amino-2-nitrophenyl)amino]-benzoic acid; 2-chloro-6-ethylamino-4-nitrophenol; 2-amino-6-chloro-4-nitrophenol; 4-[(3-hydroxypropyl)-amino]-3-nitrophenol; 2,5-diamino-6-nitropyridine; 1,2,3,4-tetrahydro-6-nitro-quinoxaline; 4-amino-2-nitro-diphenylamine (HC red No. 1); 4-amino-1-[(2-hydroxyethyl)amino-2-nitrobenzene (HC red No. 3); 1-amino-4-[(2-hydroxyethyl)amino]-2-nitrobenzene (HC red No. 7); 1-amino-5-chloro-4-[(2,3-dihydroxypropyl)amino]-2-nitrobenzene (HC red No. 10); 5-chloro-1,4-[di(2,3-dihydroxypropyl)amino]-2-nitrobenzene (HC red No. 11); 1-amino-4-[di(2-hydroxyethyl)amino-2-nitrobenzene hydrochloride (HC red No. 13); 7-amino-3,4-dihydro-6-nitro-2H-1,4-benzoxazine (HC red No. 14); 4-[(3-hydroxypropyl)amino]-3-nitrophenol (HC red BN); 1-amino-3-methyl-4-[(2-hydroxyethyl)amino]-6-nitrobenzene (HC Violet No. 1); 1-(3-hydroxypropylamine)-4-[di(2-hydroxyethyl)amino]-2-nitrobenzene (HC Violet No. 2); 1-(2-hydroxyethyl)amino-2-nitro-4-[di(2-hydroxyethyl) aminobenzene (HC Blue No. 2); 1-methylamino-4-[methyl-(2,3-dihydroxypropyl)amino]-2-nitrobenzene (HC Blue No. 6); 1-[(2,3-dihydroxypropyl)amino]-4-[ethyl-(2-hydroxyethyl)amino]-2-nitrobenzene hydrochloride (HC Blue No. 9); 1-[(2,3-dihydroxypropyl)amino]-4-[methyl-(2-hydroxyethyl)amino]-2-nitrobenzene (HC Blue No. 10); 4-[di(2-hydroxyethyl)amino]-1-[(2-methoxyethyl)amino-2-nitrobenzene (HC Blue No. 11); 4-[ethyl-(2-hydroxyethyl)amino]-1-[(2-hydroxyethyl)amino]-2-nitrobenzene hydrochloride (HC Blue No. 12); 2-((4-amino-2-nitrophenyl)amino)-5-dimethylaminobenzoic acid (HC Blue No. 13); N,N-dimethyl-3-{[4-(methylamino)-9,10-dioxo-9,10-dihydro-1-anthracenyl]-amino}-N-propyl-1-propanaminium bromide (HC Blue No. 16);

basic dyes, such as:

2-[2-((2,4-dimethoxyphenyl)amino)ethenyl]-1,3,3-trimethyl-3H-indol-1-ium chloride (C.I. 48055; basic yellow 11); 3-methyl-1-phenyl-4-[(3-(trimethylammonium)phenyl) azo]-pyrazol-5-one-chloride (C.I. 12719; basic yellow 57); 1-methyl-4-((methylphenylhydrazono)methyl)-pyridinium methylsulphate (basic yellow 87); 2-[(4-aminophenyl)azo]-1,3-dimethyl-1H-imidazolium chloride (basic orange 31); 3,7-diamino-2,8-dimethyl-5-phenylphenazinium chloride (C.I. 50240; basic red 2); 1,4-dimethyl-5-[(4-(dimethylamino)phenyl)azo]-1,2,4-triazolium chloride (C.I. 11055; basic red 22); 2-[((4-dimethylamino)phenyl)azo]-1,3-dimethyl-1H-imidazolium chloride (basic red 51); 2-hydroxy-1-[(2-methoxyphenyl)azo]-7-(trimethylammonium)-naphthalin-chloride (C.I. 12245; basic red 76); bis[4-(dimethylamino)phenyl][4-(methylamino)phenyl] carbenium-chloride (C.I. 42535; basic violet 1); tris[4-(dimethylamino)phenyl]carbenium-chloride (C.I. 42555; basic violet 3); 2-[3,6-(diethylamino)dibenzopyranium-9-yl]-benzoic acid chloride (C.I. 45170; basic violet 10); di(4-aminophenyl)(4-amino-3-methylphenyl)carbenium-chloride (C.I. 42510; basic violet 14); 9-(dimethylamino)-benzo [a]phenoxazin-7-ium-chloride (C.I. 51175; basic blue 6); di[4-(diethylamino)phenyl][4-(ethylamino)naphthyl]carbenium-chloride (C.I. 42595; basic blue 7); 3,7-di(dimethylamino)phenothiazin-5-ium-chloride (C.I. 52015; basic blue 9); 1-methylamino-4-(amino-N-propyltrimethylammonium) anthraquinone methylsulphate (C.I. 61512; basic blue 22); di[4-(dimethylamino)phenyl][4-(phenylamino)naphthyl] carbenium-chloride (C.I. 44045; basic blue 26); 2-[(4-(ethyl (2-hydroxyethyl)amino)phenyl)azo]-6-methoxy-3-methyl-benzothiazol-methylsulphate (C.I. 11154; basic blue 41); 4-[(2,6-dichlorophenyl) (4-imino-3,5-dimethyl-2,5-cyclohexadien-1-ylidene) methyl]-2,6-dimethylaniline phosphate (1:1) (C.I. basic blue 77); 3-[(4-amino-6-bromo-5,8-dihydro-1-hydroxy-8-imino-5-oxo-2-naphthalenyl)amino-N,N,N-trimethylbenzenaminium chloride (C.I. 56059; basic blue 99); bis[4-(diethylamino)phenyl]phenylcarbenium hydrogen sulphate (1:1) (C.I. 42040; basic green 1); 1,3-bis[(2,4-diamino-5-methylphenyl)azo]-3-methylbenzene (C.I. 21010; basic brown 4); 1-[(4-aminophenyl)azo]-7-(trimethylammonium)-2-naphthol-chloride (C.I. 12250; basic brown 16); 1-[(4-amino-2-nitrophenyl)azo]-7-(trimethylammonium)-2-naphthol-chloride (C.I. 12251; basic brown 17);

dispersion dye compounds in dispersion, such as:

1,4-di[(2,3-dihydroxypropyl)amino]-9,10-anthracenedione, 2-[(2-aminoethyl)amino-9,10-anthracenedione, 1-[(3-aminopropyl)amino-9,10-anthracenedione, 1,4-diamino-2-methoxy-9,10-anthracenedione (C.I. 62015, dispersed red 11); 1-amino-4-hydroxy-9,10-anthracenedione (C.I. 60710, dispersed red 15); 1,4-diamino-9,10-anthracenedione (C.I. 61100, dispersed violet 1); 1-amino-4-(methylamino)-9,10-anthracenedione (C.I. 61105, dispersed violet 4); 1,4-diamino-5-nitro-9,10-anthracenedione (C.I. 62030, dispersed violet 8); 1,4,5,8-tetraamino-anthraquinone (C.I. 64500; dispersed blue 1); 1-[(2-hydroxyethyl)amino]-4-methylamino-9,10-anthracenedione (C.I. 61505, dispersed blue 3), 1,4-dihydroxy-5,8-bis[(2-hydroxyethyl)amino-9,10-anthracenedione (C.I. 62500, dispersed blue 7); 1,4-bis[(2-hydroxyethyl)amino]-9,10-anthracenedione (C.I. 61545; dispersed blue 23); 1-[(2-hydroxyethyl)amino]-4-[(3-hydroxypropyl)amino-9,10-anthracenedione; 1,4-bis[(3-hydroxypropyl)amino]-9,10-anthracenedione;

and also:

2-((4-(acetylamino)phenyl)azo)-4-methylphenol (C.I. 11855; disperse yellow 3); 1-(4'-aminophenylazo)-4-nitrobenzene (C.I. 11005; disperse orange 3); 1-[di(2-hydroxyethyl)amino]-3-methyl-4-[(4-nitrophenyl)azo]-benzene (C.I. 11210, disperse red 17) and 4-((4-(di(2-hydroxyethyl)amino) phenyl)azo)-aniline (disperse black 9).

The following dyes, described in the third edition of the Colour Index International, can be included among the direct azo dyes:

acid yellow 1; acid yellow 9; acid yellow 23; acid yellow 36; acid orange 7; acid orange 24; acid red 33; acid red 35; acid red 92; acid violet 43; acid violet 49; acid blue 1; acid blue 3; acid blue 9; acid blue 62; acid black 1.

These colouring compounds can be contained in the dye according to the invention in amounts ranging from approx. 0.1 to 4.0% by weight.

The natural direct dyes which can be used according to the invention include, for example, those based on lawsone, juglone, alizarine, purpurine, carminic acid, kermesic acid, purpurogallin, protocatechualdehyde, indigo, isatin, turmeric, spinulosine and apigenidine. Extracts or decoctions containing these natural dyes and, in particular, henna-based compresses or extracts, can also be used.

For further typical dyeing compounds, express reference can be made to the "Dermatology" series edited by Ch. Culnan and H. Maibach, Verlag Marcel Dekker Inc., New York, Basel, 1986, volume 7, Ch. Zviak; "The Science of Hair Care", chapter 7, pp. 248-250 (substantive dyes) and chapter 8, pp. 264-267 (oxidative dyes); and to the "European Inventory of Cosmetic Raw Materials", published by the European Union, obtainable on disc from Bundesverband Deutscher Industrie—und Handelsunternehmen für Arzneimittel, Reformwaren und Körperpflegemittel e.V., Mannheim.

When the colourant is mixed with the oxidant, which in most cases is acidic (pH approx. 2 to 6.5), the pH of the ready-for-use dyes according to the invention acquires a value determined by the amount of alkali in the colourant and the amount of acid in the oxidant, and by the mixing ratio. Depending on their composition, the ready-for-use dyes can be weakly acid, neutral or alkaline and have a pH ranging from approx. 3 to 11.

The colourants according to the present invention can also contain one or more natural or synthetic additives, commonly used in solutions, creams, emulsions, gels or foam aerosols, powders and granulates, for example solvents, such as water, monohydroxy or polyhydroxy aliphatic alcohols with low molecular weight, their esters and ethers, such as alkanols, in particular with an alkyl chain comprising 1 to 4 carbon atoms, such as ethanol, n-propanol, isopropanol, butanol and isobutanol; bivalent or trivalent alcohols, in particular having 2 to 6 carbon atoms, such as ethylene glycol, propylene glycol, 1,3-propanediol, 1,4-butanediol, 1,5-pentanediol, 1,6-hexanediol, 1,2,6-hexanetriol, glycerin, diethylene glycol, dipropylene glycol, polyalkylene glycols, such as triethylene glycol, polyethylene glycol, tripropylene glycol and polypropylene glycol; low molecular weight alkyl ethers of multivalent alcohols, such as ethylene glycol monomethyl ether, ethylene glycol monoethyl ether, ethylene glycol monopropyl ether or ethylene glycol monobutyl ether, diethylene glycol monomethyl ether or diethylene glycol monoethyl ether, triethylene glycol monomethyl ether or triethylene glycol monoethyl ether; ketones and keto alcohols, in particular with 3 to 7 carbon atoms, such as acetone, methyl ethyl ketone, diethyl ketone, methyl isobutyl ketone, methyl phenyl ketone, cyclopentanone, cyclohexanone and diacetone alcohol; ethers such as dibutyl ether, tetrahydrofuran, dioxane or diisopropylether; esters such as ethyl formate, methyl formate, methyl acetate, ethyl acetate, propyl acetate, butyl acetate, phenyl acetate, ethylene glycol monoethyl ether acetate or acetic acid hydroxy ethyl ester; amides such as N-methylpyrrolidone; urea, tetramethyl urea and thiodiglycol; humidifying agents or emulsifiers selected from anionic, cationic, non-ionogenic, amphoteric or zwitterionic agents, surfactants, such as fatty alcohol sulphates, alkylsulphonates, alkylbenzene sulphonates, alklymethyl ammonium salts, alkylbetaine, α-olefin sulphonates, ethoxylated fatty alcohols, ethoxylated nonylphenols, fatty acid alkanolamines, ethoxylated esters of fatty acids, polyglycol ether sulphates of fatty acids, alkylpolyglycosides; thickeners, such as higher fatty alcohols, starch, cellulose derivatives, vaseline, paraffin oil, fatty acids and other fatty components in emulsified form, water-soluble polymer thickeners, such as natural gums, guar gum, xanthan gum, carob flour, pectin, dextran, agar-agar, amylose, amylopectin, dextrin, synthetic clays or hydrocolloids, such as polyvinyl alcohol; and conditioning agents such as lanolin derivatives, cholesterol, pantothenic acid, water-soluble cationic polymers, protein derivatives, provitamins, vitamins, plant extracts, sugar and betaine; auxiliary agents such as electrolytes, antioxidants, fatty amides, sequestering agents, film-forming agents and preservatives, and beeswax.

In this case, it can be particularly advantageous to add to the hair colourants according to the invention non-ionic and/or anionic emulsifiers or surfactants, such as fatty alcohol sulphates, in particular lauryl sulphate, sodium cocoyl sulphate; ethoxylated fatty alcohol sulphates, in particular sodium lauryl ether sulphates with 2 to 4 molecular units of ethylene oxide, ethoxylated fatty acid esters, ethoxylated nonylphenols, ethoxylated fatty alcohols, alkylbenzene sulphonates or alkanolamides of fatty acids, preferably in the total amount of approx. 0.1 to 30% by weight, and more preferably 0.2 to 15% by weight.

Examples of useful cationic surfactants are quaternary ammonium compounds; ammonium halides such as alkyltrimethylammonium chlorides, dialkyldimethylammonium chlorides and trialkylmethylammonium chlorides. Specific examples are cetyltrimethylammonium chloride, stearyltrimethylammonium chloride, distearyldimethylammonium chloride, lauryldimethylammonium chloride, lauryldimethylbenzylammonium chloride and tricetylmethylammonium chloride. Other useful cationic surfactants according to the present invention are hydrolysed quaternised proteins.

As well as non-ionic organic thickeners with properties similar to wax and non-ionic surfactants, the dye can include the usual cosmetic cationic resins; particularly preferred are Polyquaternium-6 (poly(dimethyldiallylammonium chloride)), Polyquaternium-7 (diethyldiallylammonium chloride/acrylamide copolymer), Polyquaternium-10 (cationic cellulose), Polyquaternium-11 (N,N-dimethylaminoethylmethacrylic acid/PVP copolymer diethyl sulphate), Polyquaternium-35 and Polyquaternium-37 (trimethylaminoethyl methacrylate chloride polymer), alone or mixtures thereof. The total amount of said cationic resins in the dye can range from approx. 0.1 to 6% by weight.

For the use as oxidative hair colourants, the dye compositions are mixed with an oxidative solution immediately before dyeing the hair, and a sufficient amount of ready-for-use hair colouring mixture, generally approx. 60 to 200 grains according to the thickness and amount of the hair, is applied.

The mixture is left on the hair for 10 to 45 minutes at the temperature of 5 to 50° C., preferably for 30 minutes at 30° C.; the hair is then rinsed with water and dried. If necessary, the hair is washed with shampoo after rinsing and optionally rinsed again with a weak organic acid, such as an aqueous solution of tartaric acid. The hair is then dried.

The hair colourants according to the invention provide an intensive, protective, delicate hair colour. Due to improved colour balancing, the hair can be dyed from the undamaged root to the severely damaged tip.

The dyeing results, expressed in L*a*b* values, obtained from the following examples, were measured with a Minolta Chroma Meter CR-200 colorimeter.

In the colour space L*a*b*, L* indicates lightening and a* and b* are the colour coordinates. a* and b* indicate the colour directions: +a* is the direction of red, −a* is the direction of green, +b* is the direction of yellow and −b* is the direction of blue.

Differences in colour can be expressed by the ΔE values, which are defined by the following equation:

$$\Delta E = [(\Delta L^*)^2 + (\Delta a^*)^2 + (\Delta b^*)^2]^{1/2}$$

All the alkanolamine-saccharine combinations according to the present invention have demonstrated excellent compatibility with other cosmetic ingredients and dyes, without detectably stressing the cosmetic composition; the advantages compared with compositions containing amino acids are therefore evident.

The oxidative hair dyes according to the invention offer numerous advantages. The buffer system incorporated in oxidative hair dyes produces a high lightening effect (lightening effect with low amounts of alkanolamine) with reduced irritation of the scalp and no unpleasant odour.

The examples given below further illustrate the invention.

EXAMPLES

The developer, which represents a typical standard composition and which is widely used (not inventive), is composed as indicated in Table 1.

TABLE 1

| Developer composition (9% hydrogen peroxide content) | |
| --- | --- |
| Cetearyl alcohol | 2.00 |
| Ceteareth-50 | 0.50 |
| 85% phosphoric acid | 0.10 |
| 35% hydrogen peroxide | 25.70 |
| Water | 71.70 |
| pH | 3.0 |

Example 1

Evaluation of Lightening Effect (Standard Alkalisers, No Dyes)

The following compositions were prepared, mixed 1:1 (w/w) with a standard developer composition containing 9% hydrogen peroxide, and applied to untreated human hair, shade 7/0 (medium blonde). After processing for 30 minutes at 30° C., hair samples were rinsed and dried. The results are set out in Table 2.

TABLE 2

| Type of cosmetic composition | Example 1*) solution 25% ammonium hydroxide low amount | Example 2*) solution 25% ammonium hydroxide high amount | Example 3*) solution MEA low amount | Example 4*) solution MEA high amount | Example 5 solution MEA/saccharine |
| --- | --- | --- | --- | --- | --- |
| Sodium sulphite | 0.30 | 0.30 | 0.30 | 0.30 | 0.30 |
| Ascorbic acid | 0.30 | 0.30 | 0.30 | 0.30 | 0.30 |
| EDTA | 0.20 | 0.20 | 0.20 | 0.20 | 0.20 |
| Saccharine | — | — | — | — | 10.00 |
| 25% ammonium hydroxide | 2.43 | 10.00 | — | — | — |
| Ethanolamine (MEA) | — | — | 1.13 | 8.97 | 8.97 |
| Water | 96.77 | 89.20 | 98.07 | 90.23 | 76.90 |
| pH of Composition | 10.25 | 11.03 | 10.26 | 11.27 | 10.25 |
| pH of Composition + Developer | 9.45 | 10.14 | 9.30 | 10.20 | 9.95 |
| L*a*b* before | 32.85; 7.30; 12.77 | 32.85; 7.30; 12.77 | 32.85; 7.30; 12.77 | 32.85; 7.30; 12.77 | 32.85; 7.30; 12.77 |
| L*a*b* after | 37.47; 7.29; 14.39 | 42.68; 8.76; 18.86 | 35.64; 7.31; 13.53 | 41.72; 9.03; 18.86 | 41.21; 9.86; 19.83 |
| ΔE | 4.90 | 11.66 | 2.89 | 10.90 | 11.24 |
| Odour | − | −− | ○ | ○ | ○ |
| Lightening effect | ○ | ++ | − | +/++ | ++ |
| Quality of hair, after 5 treatments | + | + | − | −− | ○/+ |
| Overall evaluation | 0 | 1 | −2 | −0.5 | 2.5 |
| Score (1 = best; 5 = worst) | 3 | 2 | 5 | 4 | 1 |

*): comparative example, not forming part of the invention

Evaluation of Results Shown in Table 2

Example 5 shows that the lightening is at the level of Examples 2 and 4, at a lower pH. Unlike example 2, example 5 has no odour of ammonia; unlike example 4, the amount of free alkanolamine is cosmetically more advantageous.

Example 2

Effect of Buffer System on Stability of Cream Compositions

The following compositions were prepared, mixed 1:1.5 (w/w) with 9% hydrogen peroxide and applied to white yak hair. After application for 30 minutes at 30° C., the samples were rinsed and dried. The results are set out in Table 3.

TABLE 3

| | Example 6*) | Example 7*) | Example 8 | Example 9 |
| --- | --- | --- | --- | --- |
| Buffer system | cream MEA/Glycine | cream MEA/Glycine | cream MEA/Saccharine | cream MEA/Tris/Saccharine |
| Cetearyl alcohol | 18.00 | 18.00 | 18.00 | 18.00 |
| Lauryl/Myristyl alcohol | 3.00 | 3.00 | 3.00 | 3.00 |
| Ceteareth-50 | 3.00 | 3.00 | 3.00 | 3.00 |
| Glyceryl stearate | 2.00 | 2.00 | 2.00 | 2.00 |

TABLE 3-continued

|  | Example 6*) | Example 7*) | Example 8 | Example 9 |
|---|---|---|---|---|
|  | Type of cosmetic composition | | | |
| Buffer system | cream MEA/Glycine | cream MEA/Glycine | cream MEA/Saccharine | cream MEA/Tris/Saccharine |
| Cocamidopropyl betaine | 10.00 | 10.00 | 10.00 | 10.00 |
| Sodium sulphite | 0.30 | 0.30 | 0.30 | 0.30 |
| Ascorbic acid | 0.30 | 0.30 | 0.30 | 0.30 |
| EDTA | 0.20 | 0.20 | 0.20 | 0.20 |
| Saccharine | — | — | 10.00 | 10.00 |
| Glycine | 10.00 | 4.10 | — | — |
| Ethanolamine (MEA) | 15.53 | 10.73 | 11.37 | 1.00 |
| Tromethamine (Tris) | — | — | — | 11.60 |
| 2,5-diaminotoluene sulphate | 3.50 | 3.50 | 3.50 | 1.30 |
| Resorcinol | 1.30 | 1.30 | 1.30 | 0.40 |
| m-Aminophenol | 0.30 | 0.30 | 0.30 | 0.08 |
| 2,4-Diaminophenoxy-ethanol 2HCl | 0.20 | 0.20 | 0.20 | 0.01 |
| 2-Methylresorcinol | — | — | — | 0.30 |
| Water | 35.47 | 45.47 | 38.93 | 38.51 |
| Observation | separation into organic and aqueous layer | separation into organic and aqueous layer | formation of cream | formation of cream |
| pH of Composition + Developer | —/— | —/— | 9.4 | 7.8 |
| Shade | —/— | —/— | Black | Medium blonde |

*): comparative example, not forming part of the invention

Evaluation of Results Shown in Table 3

Example 6 (comparative example), containing a large amount of dye and consequently a large amount of glycine, was designed to obtain a black shade. The mixture did not lead to the formation of a cream. When the amount of glycine was reduced to 4.1%, a similar result was obtained, and no cream was formed.

Unlike those examples, example 7 according to the invention, which contains a large amount of dye and 10% saccharine, does produce a stable cream.

Example 3

Liquid And Gel Compositions

The following compositions were prepared, mixed 1:1.5 (w/w) with 9% hydrogen peroxide and applied to white yak hair. After processing for 30 minutes at 30° C., the samples were rinsed and dried. The results are set out in Table 4.

TABLE 4

|  | Example 10 | Example 11 | Example 12 | Example 13 |
|---|---|---|---|---|
|  | Type of cosmetic composition | | | |
| Buffer system | Liquid AMP/Saccharine | Liquid AMP/Tris/Saccharine | Gel MEA/Saccharine | Gel Tris/Saccharine |
| Oleic acid | 12.00 | 12.00 | 16.00 | 16.00 |
| Undeceth-3 | 8.00 | 8.00 | — | — |
| Laureth-2 | 6.00 | 6.00 | 25.00 | 25.00 |
| PEG-15 Cocopolyamine | 2.00 | 2.00 | — | — |
| Ethanol | 12.00 | 12.00 | — | — |
| Propylene glycol | 5.00 | 5.00 | — | 5.00 |
| Quaternium-80 | 1.00 | 1.00 | 1.00 | — |
| Cetrimonium chloride | 2.00 | 2.00 | — | 2.00 |
| Glycol distearate | — | — | 4.00 | 4.00 |
| Sodium laureth sulphate | — | — | 5.00 | 5.00 |
| Sodium sulphite | 0.30 | 0.30 | 0.30 | 0.30 |
| Ascorbic acid | 0.30 | 0.30 | 0.30 | 0.30 |
| EDTA | 0.20 | 0.20 | 0.20 | 0.20 |
| Saccharine | 5.00 | 5.00 | 5.00 | 5.00 |
| Ethanolamine (MEA) | — | — | 7.90 | — |
| 2-Amino-2-methyl-1-propanol (AMP) | 7.50 | 4.20 | — | — |
| Tromethamine (Tris) | — | 4.50 | — | 16.50 |

TABLE 4-continued

| Buffer system | Example 10 Liquid AMP/ Saccharine | Example 11 Liquid AMP/Tris/ Saccharine | Example 12 Gel MEA/ Saccharine | Example 13 Gel Tris/ Saccharine |
|---|---|---|---|---|
| 2,5-Diaminotoluene sulphate | — | — | — | 1.60 |
| 2-Methoxymethyl-p-phenylenediamine | — | 0.15 | — | — |
| Resorcinol | — | 0.07 | — | 0.80 |
| m-Aminophenol | — | 0.01 | — | 0.07 |
| 3-Amino-2,6-dimethyl-phenol | — | 0.01 | — | — |
| 4-Aminophenol | 0.60 | — | — | — |
| 4,5-Diamino-1-hydroxy-ethylpyrazole sulphate | — | — | 1.70 | — |
| 3-Amino-6-methylphenol | 0.35 | — | 1.10 | — |
| 2-Methylresorcinol | 0.50 | 0.02 | — | — |
| 2,4-Diaminophenoxy-ethanol 2HCl | — | — | — | 0.02 |
| Water | 37.25 | 37.24 | 32.50 | 18.21 |
| pH of Composition + Developer | 8.2 | 8.0 | 9.2 | 8.2 |
| Shade | Golden red | Light blonde | Deep red | Natural ash Medium brown |

Evaluation of Results Shown in Table 4

Examples 10-13 demonstrate the high compatibility of the buffer system according to the invention with liquid and gel compositions which are usually highly sensitive to the amount of salt.

The invention claimed is:

1. An oxidative hair colour composition comprising a buffer system consisting of saccharine and at least one alkanolamine.

2. An oxidative hair colour composition according to claim 1, wherein the alkanolamine has general formula Ia:

$$H_2N\text{---}(Y)\text{---}OH \quad\quad (Ia)$$

wherein Y is a straight or branched aliphatic diradical containing 2 to 5 carbon atoms optionally substituted by one or two further hydroxy groups.

3. An oxidative hair colour composition according to claim 1, wherein the alkanolamine is selected from the group consisting of monoethanolamine, 1-amino-2-propanol, 2-amino-2-methyl-propanol (AMP), 2-amino-2-methyl-1,3-propanediol, 2-amino-2-ethyl-1,3-propanediol and tris(hydroxymethyl)-aminomethane.

4. An oxidative hair colour composition according to claim 1, wherein the alkanolamine ranges from 0.1 to 17% by weight.

5. An oxidative hair colour composition according to claim 4, wherein the alkanolamine ranges from 2 to 10% by weight.

6. An oxidative hair colour composition according to claim 1, wherein the saccharine ranges from 0.1 to 17% by weight.

7. An oxidative hair colour composition according to claim 6, wherein the saccharine ranges from 2 to 6% by weight.

8. An oxidative hair colour composition according to claim 1, wherein the saccharine is in free acid form and the alkanolamine is in free base form, or either the saccharine or at least one alkanolamine is in salt form, or saccharine and at least one alkanolamine are in salt form.

9. An oxidative hair colour composition according to claim 1, wherein the molar ratio between alkanolamine, or its salt, and saccharine, or its salt, ranges from 1:1 to 10:1.

10. An oxidative hair colour composition according to claim 1, having a pH of 8 to 11.

* * * * *